United States Patent [19]
Ong

[11] 4,195,084
[45] Mar. 25, 1980

[54] TASTE-STABLE AQUEOUS PHARMACEUTICAL SUSPENSION OF TALL OIL SITOSTEROLS AND A METHOD FOR THE PREPARATION THEREOF

[75] Inventor: John T. H. Ong, Indianapolis, Ind.

[73] Assignee: Eli Lilly and Company, Indianapolis, Ind.

[21] Appl. No.: 918,113

[22] Filed: Jun. 22, 1978

Related U.S. Application Data

[63] Continuation of Ser. No. 757,711, Jan. 7, 1977, abandoned.

[51] Int. Cl.² ............................................. A61K 31/56
[52] U.S. Cl. .................................. 424/238; 424/362; 424/365
[58] Field of Search ....................................... 424/238

[56] References Cited

U.S. PATENT DOCUMENTS 3,934,034   1/1976   Manning ............................... 424/346

OTHER PUBLICATIONS

Physicians Desk Reference (P.D.R.) 26th ed., 1972 p. 844.
Merck Index 9th ed., p. 1105 (1976).
Remington's Pharmaceutical Sciences, 13th ed., pp. 213,214,220,445,446,1407–1418 (1965).

Primary Examiner—Leonard Schenkman
Attorney, Agent, or Firm—Leroy Whitaker; Arthur R. Whale

[57] ABSTRACT

A pharmaceutical preparation is described which comprises a taste-stable aqueous suspension of tall oil sitosterols.

A method is provided for preparing such a suspension.

11 Claims, No Drawings

TASTE-STABLE AQUEOUS PHARMACEUTICAL SUSPENSION OF TALL OIL SITOSTEROLS AND A METHOD FOR THE PREPARATION THEREOF

This is a continuation of application Ser. No. 757,711 filed Jan. 7, 1977, now abandoned.

BACKGROUND OF THE INVENTION

This invention relates to a pharmaceutical preparation for oral administration. Specifically, this invention is concerned with an aqueous suspension of tall oil sitosterols (essentially β-sitosterol) and a method for the preparation of such a suspension.

DESCRIPTION OF THE PRIOR ART

Sitosterols, when administered orally to man, are known to cause a lowering of serum cholesterol. For almost two decades, physicians have been prescribing sitosterols for hypercholesterolemic patients. The sitosterols available for such prescribing have been obtained from soy oil. Sitosterols, along with many other plant sterols, occur naturally in oils of vegetable origin.

It has been known that the most effective of the sterols for lowering serum cholesterol is β-sitosterol. About 60 percent of the total refined sterols obtained from soy oil is β-sitosterol. Other vegetable oils yield varying quantities of β-sitosterol in the total sterols recoverable from the oil.

Because of certain physical properties of the sterols it has not been practical to provide a pharmaceutical suspension for oral administration which contains much more than 20 percent W/V of sitosterols. This condition, coupled with a dosage regimen as high as 24 to 36 grams of sitosterols per day, results in a rather bulky and cumbersome quantity of medication to be taken by the patient. Moreover, because of the manner in which sitosterols are effective in lowering serum cholesterol, the medicament should be taken orally along with meals.

Furthermore, in order for sitosterols to be the most effective in lowering serum cholesterol, the medicament must reach the gastrointestinal tract in a finely divided dispersed state.

Additionally, while sitosterols are essentially tasteless, because of their oily or waxy characteristic they do not lend themselves readily to incorporation into an aqueous preparation for oral administration that has a pleasant mouth feel.

Accordingly, it is an object of this invention to provide an aqueous pharmaceutical suspension of sitosterols in which essentially all of the sitosterols are present as β-sitosterol, the most effective form of sitosterols for lowering serum cholesterol.

Another object of this invention is to provide an aqueous pharmaceutical suspension of sitosterols which has an acceptable taste and mouth feel which is retained by the suspension for an indefinite storage period.

SUMMARY

It has now been discovered that an aqueous pharmaceutical suspension comprised of (a) finely divided tall oil sitosterols; (b) a pharmaceutically acceptable chelating agent; (c) sodium carboxymethylcellulose; (d) sorbitol; (e) a pharmaceutically acceptable surfactant; (f) simethicone; and, (g) water contains sitosterols of which 80 percent or more is β-sitosterol, and has an acceptable taste and mouth feel that does not change over an extended storage period.

DESCRIPTION OF THE PREFERRED EMBODIMENTS

One aspect of this invention relates to a novel aqueous pharmaceutical preparation for oral administration which contains sitosterols, of which 80 percent or more is β-sitosterol, dispersed as very finely divided particles in a suitable pharmaceutical vehicle. This useful pharmaceutical preparation is comprised of: (a) finely divided tall oil sitosterols; (b) a pharmaceutically acceptable chelating agent, or combination of agents; (c) sodium carboxymethylcellulose; (d) sorbitol; (e) a pharmaceutically acceptable surfactant selected from the class consisting of polyoxyethylene (20) sorbitan monolaurate, polyoxyethylene (20) sorbitan monopalmitate, polyoxyethylene (20) sorbitan monooleate, polyoxyethylene (20) sorbitan monostearate and sodium lauryl sulfate; (f) simethicone; and (g) water.

Tall oil sitosterols are a fraction of tall oil. Tall oil is a resinous by-product from the manufacture of chemical wood pulp. It is used in making soaps, coatings and machine oils. The sterol fraction is generally present as a minor constituent of tall oil and is usually concentrated and isolated from the residue from the oil after the substances useful in making soaps, etc. have been removed. The sterol fraction of tall oil is especially rich in β-sitosterol, the most effective sitosterol for lowering serum cholesterol. Eighty percent or more of the tall oil sterols fraction is comprised of β-sitosterol.

Sitosterols is specified in National Formulary XIII (1970) as a mixture of β-sitosterol and related sterols of plant origin. [Sitosterols was not admitted to N. F. XIV (1975)] The material contains not less than 95 percent of total sterols and not less than 85 percent of unsaturated sterols, calculated on a dry basis as β-sitosterol. The principal active ingredient in sitosterols N. F. XIII is β-sitosterol. It is an unsaturated sterol. Other unsaturated sterols include campesterol and stigmasterol. Chemically, β-sitosterol is described as stigmast-5-en-3β-ol ($C_{29}H_{50}O$).

An essential element in the effectiveness of the tall oil sitosterols in the lowering of serum cholesterol is the administration of the active agent in a very finely divided form. To accomplish this, the tall oil sitosterols are ground in a high energy mill to a means particle size of 25 microns or below, with 99 plus percent of the particles passing a 325 mesh U.S. screen (44 micron openings). The tall oil sitosterols can be reduced to this particle size by milling in an air mill, a high energy hammer mill, or an air attrition mill. In the case of the high energy hammer and air attrition mills, it is necessary to provide refrigeration in the milling operation to succesfully reduce the particle size to the desired range. One way that this refrigeration can be provided is to finely grind dry ice and physically mix such ice with the tall oil sitosterols as the feed stock is being introduced into the mill.

The novel aqueous pharmaceutical suspension of this invention can contain up to about 25 percent (W/V) of finely divided tall oil sitosterols. Actually, the range can be from >0 to about 25 percent, but practically anything below 10 percent is not really a useful concentration. So it can be stated that the range of the tall oil sitosterols concentration in the suspension is between about 10 and about 25 percent. In effect, because of the aforementioned need for large daily intakes of β-sitosterol to alleviate hypercholesterolemia, the tall oil sitosterols content should be as high as is consistent with pharmaceutical elegance and stability. It was determined that at about 20 percent tall oil sitosterols the suspension is not excessively viscous, is relatively easy to pour and has both good physical and chemical stability. A 20 percent tall oil sitosterols content is the preferred concentration in an aqueous suspension.

Soy oil has been the source of the sitosterols employed in the commercial product prescribed for the past two decades for lowering serum cholesterol. The sitosterols obtained from soy oil have been found to contain only about 60 percent $\beta$-sitosterol, the most effective of the sitosterols for lowering serum cholesterol. Repeated efforts to upgrade such sitosterols to increase the $\beta$-sitosterol content have not been successful.

It has been known for quite some time that tall oil sitosterols are rich in $\beta$-sitosterol. Only recently, however, has an economical process been developed to isolate and purify such sitosterols so that they can be used in a pharmaceutical suspension for oral administration.

When finely ground tall oil sitosterols were substituted for sterols from soy oil in the existing suspension formula there was no immediate difference noted in physical properties, taste or mouth feel. However, within two weeks at room temperature the suspension of tall oil sitosterols developed an exceptionally bitter taste. The taste of a suspension prepared with sterols from soy oil does not deteriorate over an extended time; three years or more. Subsequently, the useful composition of this invention was discovered. The tall oil sitosterols preparation as detailed above developed no taste change after one year of shelf storage at room temperature.

Incorporated with tall oil sitosterols in the useful composition of this invention are: (a) a chelating agent, (b) sodium CMC, (c) sorbitol, (d) a surfactant, (e) simethicone, and (f) water.

Pharmaceutically acceptable chelating agents such as the polyaminocarboxylic acids, represented by ethylene diamine tetraacetic acid; amino acid derivatives, such as N,N-di(2-hydroxyethyl)glycine; hydroxy acids, represented by citric acid, and alkali metal salts thereof; polyphosphates, polyhydroxy alkyl and aryl compounds, polyamines, thiocarboxylic acids, thioamines, saccharic acid, and the like, can be employed in the composition. Particularly preferred as a chelating agent is calcium disodium ethylenediaminetetraacetate (CaNa$_2$EDTA). The CaNa$_2$EDTA is employed in an amount from about 0.004 to about 0.01 percent (W/V) of the suspension. The especially preferred concentration is from about 0.008 to about 0.01 percent (W/V). Calcium disodium ethylenediaminetetraacetate is official in the United States Pharmacoperia (USP) XIX, pp. 163-4, (1975) and is named Edetate Calcium Disodium.

Sodium carboxymethylcellulose (NaCMC) is utilized in an amount of from about 0.5 to about 2.0 percent (W/V) of the suspension. The grade of NaCMC especially preferred is NaCMC330 and the preferred concentration in the suspension is about 1.0 percent (W/V).

Sorbitol is added to the suspension as a 70 percent solution. Sorbitol Solution is official in U.S.P. XIX, p 574. From about 5.0 to about 15.0 percent (W/V) of Sorbitol Solution, preferably about 10 percent (V/V), is included in the useful composition of this invention.

One or more surfactants selected from the class consisting of polyoxyethylene (20) sorbitan monolaurate, polyoxyethylene (20) sorbitan monopalmitate, polyoxyethylene (20) sorbitan monooleate, polyoxyethylene (20) sorbitan monostearate, and sodium lauryl sulfate in an amount of from about 0.025 to about 0.075 percent (W/V) is incorporated in this useful composition. The preferred surfactant is sodium lauryl sulfate in an amount of about 0.05 percent (W/V).

The simethicone is added to the suspension as an emulsion. It is an antifoam agent. It is official in the National Formulary XIV (NF XIV), p. 648, (1975). One brand of simethicone is Dow Corning's Medical Antifoam A Compound. Chemically simethicone is a dimethylpolysiloxane and is a mixture of polymers of varying molecular weights. It is a translucent, gray, viscous fluid. In this invention it is preferred to use an emulsion of the simethicone in preparing the tall oil sitosterols suspension. A 30 percent emulsion of simethicone is available from Dow Corning, Midland, Michigan under the designation, Medical Antifoam AF Emulsion. In addition to the 30 percent simethicone, the Antifoam AF Emulsion also contains 14 percent stearate emulsifiers and 0.075 percent sorbic acid, neither of the latter two ingredients being part of this invention. However, they become part of the composition of the suspension when the AF emulsion is used as the source of the simethicone. Simethicone is utilized in the composition in an amount of from about 0.015 to about 0.045 percent (W/V). The preferred amount is about 0.030 percent.

The useful pharmaceutical suspension of this invention is comprised of: (a) from about 10 to about 25 percent (W/V) finely ground tall oil sitosterols; (b) from about 0.004 to about 0.01 percent (W/V) of edetate calcium disodium; (c) from about 0.5 to about 2.0 percent (W/V) of sodium carboxymethylcellulose 330; (d) from about 5.0 to about 15.0 percent (V/V) of sorbitol solution; (e) from about 0.025 to about 0.075 percent (W/V) of a surfactant selected from the class consisting of polyoxyethylene (20) sorbitan monolaurate, polyoxyethylene (20) sorbitan monopalmitate, polyoxyethylene (20) sorbitan monooleate, polyoxyethylene (20) sorbitan monostearate, and sodium lauryl sulfate; (f) from about 0.015 to about 0.045 percent (W/V) simethicone; and, (g) water q.s. to 100 parts by volume.

The preferred composition of the novel suspension of the instant invention is comprised of: (a) about 20 percent (W/V) of tall oil sitosterols; (b) about 0.01 percent (W/V) of edetate calcium disodium; (c) about 1 percent sodium carboxymethylcellulose 330; (d) about 10 percent (V/V) of sorbitol solution; (e) about 0.05 percent (W/V) of sodium lauryl sulfate; (f) about 0.030 percent (W/V) of simethicone; and, (g) water q.s. to 100 parts by volume.

Other agents which are not a part of this useful invention are usually added to the composition to provide protection against microorganism growth, to adjust the pH, as antioxidants, and to add to the palatability of the suspension. For example, butyl paraben in an amount of from about 0.01 to 0.02 percent (W/V), and benzoic acid in an amount of from about 0.05 to about 0.15 percent (W/V) are added as antimicrobials. Butylated hydroxy anisole and butylated hydroxy toluene in an amount of from about 0.001 to about 0.002 percent (W/V) are added as antioxidants. Ethyl alcohol in an amount of from about 0.5 to about 1.5 percent (V/V) is added as a co-solvent. Citric acid in an amount of from about 0.1 to about 0.2 percent (W/V), and sodium citrate in an amount of from about 0.05 to about 0.15 percent (W/V) are added to adjust the pH. And, saccharin and flavoring (raspberry is a good one) are added to taste.

Another aspect of this invention relates to the process for preparing the novel suspension having the composition described hereinbefore.

The process by which the useful pharmaceutical suspension described hereinbefore is prepared comprises the steps of: (a) commingling the antifoam AF emulsion with about 80 to about 90 percent of the water required to complete the suspension; (b) adding with vigorous agitation the chelating agent and the surfactant to the preparation from (a); (c) adding slowly with vigorous agitation the tall oil sitosterols to the preparation from (b); (d) agitating the preparation from (c) until the tall oil sitosterols are completely dispersed; (d) adding the sodium carboxymethylcellulose to the preparation from (d) and completely hydrating the NaCMC with vigorous agitation; (f) homogenizing and deaerating the preparation from (e); and, (g) adding sufficient water to the preparation from (f) to q.s. the suspension to the desired volume.

In a preferred process of commingling the antifoam AF emulsion with the water, the water is measured into a vessel of the appropriate capacity and which is equipped with a turbine type agitator. The antifoam AF emulsion is added routinely to the water and vigorous agitation quickly achieves a thoroughly stable emulsion. In this invention it is imperative that the simethicone contained in the antifoam AF emulsion be in the vehicle before the tall oil sitosterols are added thereto as the simethicone greatly reduces the entrainment of air in the suspension and allows for a much more rapid dispersion of the sitosterols when they are added to the vehicle.

With the simethicone thoroughly distributed in the vehicle, the chelating agent and the surfactant can be added routinely to the vehicle, and a solution of the latter two ingredients is easily obtained with vigorous agitation.

With the antifoam agent, chelating agent, and surfactant evenly and thoroughly dispersed in the vehicle, the tall oil sitosterols can be suspended therein. It is preferred to add the very finely ground sitosterols slowly to the vehicle taking care that the rate of addition does not flood the surface with undispersed solids. Tall oil sitosterols are very hydrophobic and stubbornly resist wetting. Vigorous continuous agitation is required to effectively disperse the tall oil sitosterols in the vehicle.

When the suspension has been completely established as evidenced by the absence of any perceptible coalesced particles therein, the sodium carboxymethylcellulose is added with continued vigorous agitation. The NaCMC does not hydrate promptly. Considerable time may be required to complete the hydration process. A preferred method calls for gentle mixing overnight, or for eight hours, to complete the hydration.

The sorbitol solution is added after the NaCMC hydration is complete. A simple mixing suffices to incorporate the sorbitol in the suspension.

Following the addition of all of the ingredients to the water and thorough blending and wetting thereof, the aqueous dispersion containing from about 80 to about 90 percent of the water in the suspension can be q.s'd. to volume before homogenization and deaeration. However, a preferred process involves an homogenization and deaeration before q.s. to volume. This allows the use of the water for q.s. to flush the homogenizer and deaeration apparatus.

In any event the dispersion is homogenized under a pressure of approximately 5000 psig. Following homogenization, the homogenized composition is deaerated. One of the serious problems that is encountered in dispersing tall oil sitosterols in water to provide a suspension such as that described immediately above is the incorporation of significant quantities of air in the dispersion. While the dispersion of sitosterols will be deaerated to a degree merely upon standing, it is generally advisable to utilize a mechanical procedure to accomplish a more thorough degassing of the dispersion. One method of accomplishing the deaeration is to slowly flow the dispersion in a thin film over a plate in the inside of a container on which vacuum can be drawn to a pressure of $-30$ inches of mercury or more. Such an operation is generally easy to complete and will result in the removal of better than 99 percent of the air entrained in the dispersion. Essentially complete deaeration leaves the suspension easily pourable.

The preparation of a taste-stable pharmaceutical suspension containing 20 percent (W/V) of tall oil sitosterols is described in Example 1.

EXAMPLE 1

Fifteen liters of 20 percent (W/V) of tall oil sitosterols were prepared as follows:

Nine liters of purified water were placed in a suitable vessel equipped with a laboratory turbine type agitator. Fifteen grams of Antifoam AF Emulsion (30% simethicone) were added to the water and thoroughly dispersed therein. Then 1.5 grams of edetate calcium disodium and 15.0 grams of sodium lauryl sulfate were dissolved in the water-simethicone preparation. Vigorous agitation was continued.

To the vehicle described immediately above were added 3.0 kg of very finely ground tall oil sitosterols. The addition was continuous for about 5 minutes. After all of the sitosterols had been added, vigorous agitation was continued for about 45 minutes until no lumps were perceptible in the dispersion. After completing the dispersal of the tall oil sitosterols, 150 grams of sodium carboxymethylcellulose were added to the preparation. The mixing rate was reduced to a steady roll and continued overnight to effect a complete hydration of the NaCMC.

The next morning 1.5 kg of sorbitol solution was added and thoroughly blended into the preparation.

The aqueous tall oil sitosterols suspension described above was pumped through a Manton-Gaulin homogenizer under about 5000 psig pressure.

The homogenized suspension was deaerated by flowing the dispersion in a thin film over a flat plate inside a vacuum chamber with greater than $-30$ inches of mercury vacuum. This operation removed approximately 99 percent of the entrained air from the suspension. The degassed dispersion was collected in an appropriate vessel.

The resuling tall oil sitosterols suspension was a smooth, flowable bland tasting preparation which did not become bitter on storage at room temperature for one year.

What is claimed is:

1. A taste-stable aqueous pharmaceutical suspension for oral administration to reduce hypercholesteremia comprising: (a) a pharmaceutically active amount of finely ground tall oil sitosterols; (b) a pharmaceutically acceptable chelating agent in an amount sufficient to inhibit oxidative degradation of the tall oil sitosterols; (c) sodium carboxymethylcellulose; (d) sorbitol; (e) a surfactant selected from the class consisting of: polyoxyethylene (20) sorbitan monolaurate, polyoxyethylene (20) sorbitan monopalmitate, polyoxyethylene (20) sorbitan monooleate, polyoxyethylene (20) sorbitan monostearate, and sodium lauryl sulfate; (f) simethicone; and, (g) water.

2. The aqueous pharmaceutical suspension of claim 1 wherein said suspension is comprised of: (a) from about 10 to about 25 percent (W/V) of finely ground tall oil sitosterols; (b) from about 0.004 to about 0.01 percent (W/V) of a pharmaceutically acceptable chelating agent; (c) from about 0.5 to about 2.0 percent (W/V) of sodium carboxymethylcellulose; (d) from about 5.0 to about 15.0 percent (W/V) of Sorbitol Solution, U.S.P.; (e) from about 0.025 to about 0.075 percent (W/V) of surfactant selected from the class consisting of polyoxyethylene (20) sorbitan monolaurate, polyoxyethylene (20) sorbitan monopalmitate, polyoxyethylene (20) sorbitan monooleate, polyoxyethylene (20) sorbitan monostearate, and sodium lauryl sulfate; (f) from about 0.015 to about 0.045 percent (W/V) simethicone; and, (g) water q.s. to 100 parts by volume.

3. The aqueous pharmaceutical suspension of claim 1 wherein said suspension is comprised of: (a) about 20 percent (W/V) of finely ground tall oil sitosterols; (b) about 0.01 percent (W/V) of edetate calcium disodium; (c) about 1 percent (W/V) of sodium carboxymethylcellulose; (d) about 10 percent (W/V) of Sorbitol Solution, U.S.P.; (e) about 0.05 percent (W/V) of sodium lauryl sulfate; (f) about 0.03 percent (W/V) simethicone; and, (g) water q.s. to 100 parts by volume.

4. A method of preparing a taste-stable aqueous pharmaceutical suspension for oral administration to reduce hypercholesteremia comprising:
 a. commingling simethicone with water;
 b. mixing a pharmaceutically acceptable chelating agent in an amount sufficient to inhibit oxidative degradation of tall oil sitosterols, and a surfactant selected from the class consisting of polyoxyethylene (20) sorbitan monolaurate, polyoxyethylene (20) sorbitan monooleate, polyoxyethylene (20) sorbitan monostearate, and sodium lauryl sulfate, to the preparation of (a);
 c. mixing a pharmaceutically active amount of tall oil sitosterols with the preparation of (b);
 d. adding sodium carboxymethylcellulose to the preparation of (c);
 e. hydrating the sodium carboxymethylcellulose in the preparation of (d) by mixing such preparation for 8 hours or more;
 f. blending sorbitol with the preparation of (e);
 g. homogenizing the preparation from (f); and
 h. deaerating the preparation of (g).

5. The method of claim 4 wherein the chelating agent is edetate calcium disodium.

6. The method of claim 4 wherein the surfactant is sodium lauryl sulfate.

7. An aqueous pharmaceutical suspension as in claim 1 wherein the pharmaceutically acceptable chelating agent is citric acid.

8. An aqueous pharmaceutical suspension as in claim 1 wherein an antioxidant is added.

9. An aqueous pharmaceutical suspension as in claim 8 wherein the pharmaceutically acceptable chelating agent is citric acid.

10. A method of preparing an aqueous pharmaceutical suspension for oral administration comprising:
 a. combining with agitation from about 0.05 to about 0.15 parts by weight of a 30% simethicone emulsion with about 60 parts by volume of water;
 b. adding with agitation from about 0.004 to about 0.01 parts by weight of edetate calcium disodium and from about 0.025 to about 0.075 parts by weight of sodium lauryl sulfate to the combination of (a);
 c. adding with agitation from about 10 to about 25 parts by weight of very finely ground tall oil sitosterols to te combination of (b);
 d. mixing the combination of (c) until uniform;
 e. adding from about 0.5 to about 2.0 parts by weight of sodium carboxymethylcellulose to the combination of (d);
 f. hydrating the sodium carboxymethylcellulose in the combination of (e) by mixing for 8 hours or more.

11. A method of preparing an aqueous pharmaceutical suspension for oral administration comprising:
 a. combining with agitation about 0.1 partly by weight of a 30% simethicone emulsion with about 60 parts by volume of water;
 b. combining with agitation about 0.01 parts by weight of edetate calcium disodium and about 0.05 parts by weight of sodium lauryl sulfate with the combination of (a);
 c. adding with agitation about 20 parts by weight of finely ground tall oil sitosterols to the combination of (b);
 d. mixing the combination of (c) until uniform;
 e. adding about 1 part by weight of sodium carboxymethylcellulose to the combination of (d);
 f. hydrating the sodium carboxymethylcellulose in the combination of (e) by mixing for 8 hours or more;
 g. adding with agitation about 10 parts by weight of solution sorbitol (70% sorbitol) to the combination of (f);
 h. homogenizing the combination of (g);
 i. deaerating the combination of (h); and
 j. adding water to q.s. to 100 parts by volume.

* * * * *